United States Patent [19]

Myers et al.

[11] Patent Number: 4,661,602
[45] Date of Patent: Apr. 28, 1987

[54] SUBSTITUTED ALKYL IMIDAZOLE DERIVATIVES

[75] Inventors: Peter L. Myers, Aylesbury; Chris D. Floyd, Great Missendes, both of Great Britain

[73] Assignee: G. D. Searle & Co., Skokie, Ill.

[21] Appl. No.: 717,981

[22] Filed: Mar. 29, 1985

[51] Int. Cl.$^4$ .................. C07D 233/61; C07D 403/06
[52] U.S. Cl. .................... 548/336; 548/262; 548/348; 548/350; 548/355
[58] Field of Search ............... 548/350, 336, 348, 262

[56] References Cited

U.S. PATENT DOCUMENTS

| 4,107,314 | 8/1978 | Cox et al. | 548/336 X |
| 4,144,346 | 3/1979 | Heeres et al. | 548/336 X |
| 4,223,036 | 9/1980 | Heeres et al. | 548/262 X |
| 4,324,792 | 4/1982 | Bradshaw et al. | 548/336 X |
| 4,377,697 | 3/1983 | Fellner et al. | 548/336 |

FOREIGN PATENT DOCUMENTS

| 117578 | 9/1984 | European Pat. Off. | 548/341 |
| 2067993 | 8/1981 | United Kingdom | 548/341 |

OTHER PUBLICATIONS

*Drugs,* 1975, 9, 406, Sawyer, et al.

*Primary Examiner*—Richard A. Schwartz
*Attorney, Agent, or Firm*—Steven M. Odre; Richard E. L. Henderson

[57] ABSTRACT

The present invention relates to a class of novel substituted alkyl imidazole compounds that are useful as anti-anaerobic agents. The present invention further relates to pharmaceutical compositions that contain such compounds and are also useful as anti-anaerobic agents. The compounds are of the formula

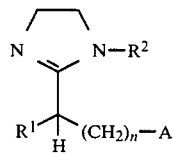

wherein A, $R^1$, $R^2$ and n are defined hereinbelow.

6 Claims, No Drawings

SUBSTITUTED ALKYL IMIDAZOLE DERIVATIVES

BACKGROUND OF THE INVENTION

The present invention relates to a class of novel substituted alkyl imidazole derivatives. The invention further relates to pharmaceutical compositions containing such compounds and to the use of such compounds and compositions as anti-anaerobic agents.

Various azole derivatives are useful as anti-fungal agents. U.S. Pat. No. 4,107,314 describes a class of heterocyclic thioalkyl substituted imidazole derivatives useful as anti-anaerobic agents. U.S Pat. Nos. 4,144,346 and 4,223,036 describe a class of 1-(1,3-dioxolan-2-yl methyl)-1H-imidazoles and 1-(1,3-dioxolan-2-ylmethyl)-1H-1,2,4 triazoles respectively, which are useful as antifungal and antibacterial agents. Miconazole, described by P. R. Sawyer, R. N. Brogden, R. M. Pinder, T. M. Speight and G. S. Avery, *Drugs*, 1975, 9, 406 is a topical and intravenous antifungal agent. European patent application No. 117578 describes a class of azole-substituted alcohol derivatives. U.K. Pat. No. 2067993 describes a class of imidazole hydrazone derivatives useful as anti-anaerobic agents. U.S. Pat. No. 4,377,697 describes a class of imidazole hydrazone and hydrazine derivatives useful as anti-anaerobic and anti-fungal agents.

SUMMARY OF THE INVENTION

The present invention relates to a class of novel compounds of the formula:

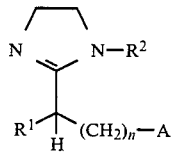

wherein

A is imidazol-1-yl, pyrazol-1-yl. 1,2,4-triazol-1-yl, 4,5-dihydroimidazol-1-yl, substituted imidazol-1-yl or substituted 4,5-dihydroimidazol-1-yl wherein the imidazol-1-yl or 4,5-dihydroimidazol-1-yl is substituted with a group selected from the class consisting of $C_1-C_4$ alkyl and $C_1-C_4$ alkylthio;

$R^1$ is phenyl or substituted phenyl having from 1 to 3 substituents independently selected from the class consisting of $C_1-C_4$ alkyl and halogen;

$R^2$ is $C_1-C_{12}$ alkyl, phenyl, substituted phenyl having from 1 to 3 substituents independently selected from the class consisting of $C_1-C_4$ alkyl, halogen and trifluoromethyl; or a

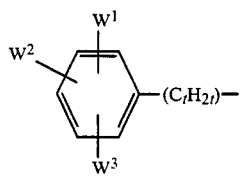

group wherein t is an integer of from 1 to 4 and $W^1$, $W^2$, and $W^3$ are independently hydrogen, $C_1-C_4$ alkyl, halogen or trifluoromethyl;

n is an integer 1 or 2;

and pharmaceutically acceptable acid addition salts thereof.

This invention further relates to pharmaceutical compositions containing the compounds of formula (I) and to the use of such compounds and compositions as anti-anaerobic agents, in particular in the treatment of peridontal disease.

In addition certain novel intermediates in the process for preparing the compounds of formula (I) are also useful as anti-anaerobic agents.

DETAILED DESCRIPTION OF THE INVENTION

The $C_1-C_4$ alkyl and $C_1-C_{12}$ alkyl groups specified herein are straight or branched chain hydrocarbon radicals having from one to four and from one to twelve carbon atoms respectively. Illustrative of such $C_1-C_4$ alkyl radicals include methyl, ethyl, propyl, isopropyl, butyl, isobutyl, sec-butyl and tert-butyl. Illustrative of such $C_1-C_{12}$ alkyl radicals include methyl, ethyl, propyl, isopropyl, butyl, isobutyl, sec-butyl, tert-butyl, pentyl, neopentyl, hexyl, isohexyl, heptyl, octyl, decyl and the like.

As used herein the term "halogen" or "halo" refers to fluoro, chloro, bromo and iodo.

The term "substituted phenyl" as used herein represents a phenyl radical having from 1 to 3 and preferably 1 or 2 substituents independently selected from the class consisting of $C_1-C_4$ alkyl, halogen and trifluoromethyl. Illustrative of such substituted phenyl radicals include methylphenyl, ethylphenyl, dimethylphenyl, (methyl)ethylphenyl, dimethylphenyl, chlorophenyl, dichlorophenyl, dibromophenyl, bromophenyl, trichlorophenyl, trifluoromethylphenyl and the like.

Representative of the groups represented by the formula

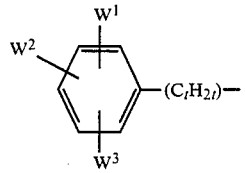

wherein t, $W^1$, $W^2$ and $W^3$ are above defined; include for example methylphenylmethyl, dimethylphenylethyl, chlorophenylpropyl, methylbromophenylmethyl, dichlorophenylpropyl, dichlorophenylmethyl, trifluoromethylphenylmethyl, trimethylphenylmethyl and the like.

The term "substituted imidazol-1-yl" and "substituted 4,5-dihydroimidazol-1-yl" refers respectively to an imidazol-1-yl or an 4,5-dihydroimidazol-1-yl radical having a substituent selected from the group consisting of $C_1-C_4$ alkyl and $C_1-C_4$ alkylthio. Representative of such substituted imidazol-1-yl and substituted 4,5-dihydroimidazol-1-yl radicals includes for example methylimidazol-1-yl, ethylimidazol-1-yl, methyl-4,5-dihydroimidazol-1-yl, t-butyl-4,5-dihydroimidazol-1-yl, isopropyl-4,5-dihydroimidazol-1-yl, methylthioimidazol-1-yl, propylthioimidazol-1-yl, methylthio-4,5-dihydroimidazol-1-yl, sec-butyl-4,5-dihydroimidazol-1-yl and the like.

The compounds of formula (I) may be prepared in accordance with one of the following synthetic routes:

METHOD A:

A substituted prop-2-enoate of the formula

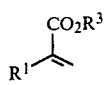
(II)

wherein $R^3$ is $C_1$–$C_4$ alkyl; is reacted with imidazole in the presence of tetramethylguanidine in an appropriate solvent to yield a substituted propanoate of the formula

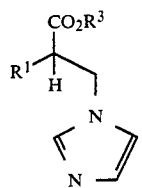
(III)

The substituted propanoate of formula (III) is hydrolyzed in the presence of an appropriate solvent to yield a 3-(imidazol-1-yl)-2-phenylpropanoic acid of the formula

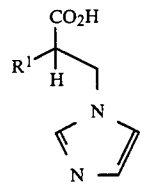
(IV)

The propanoic acid of formula (IV) is treated with an oxalyl chloride, followed by dimethylformamide. To the reaction mixture is added a substituted ethanediamine of the formula $R^2$—NH—$CH_2$—$CH_2$—$NH_2$  (V)

wherein $R^2$ is above defined; and triethylamine in the presence of dichloromethane to yield a substituted ethanediamine of the formula

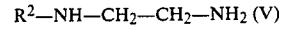
CONH(CH$_2$)$_2$NHR$^2$  (VI)

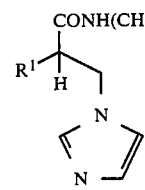

The substituted ethanediamine of formula (VI) is treated with methanesulfonic acid and phosphorous pentoxide at a temperature of from 70° C. to 150° C. in an inert atmosphere. The reaction mixture is quenched with an ice/aqueous ammonia mixture to yield a substituted 4,5-dihydro-2[2-(imidazol-1-yl)-1-(substituted)ethenyl]imidazole of formula (I).

METHOD B:

A 1-substituted-4,5-dihydro-2-substituted imidazole of the formula

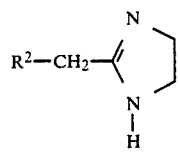
(VII)

in dimethylformamide, preferably under an inert atmosphere, is added to a suspension containing sodium hydride in dimethylformamide. To the reaction mixture is added a benzylhalide of the formula

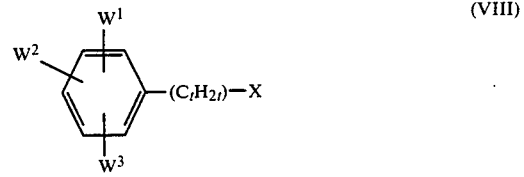
(VIII)

wherein X is halogen and $W^1$, $W^2$, $W^3$ and t are above defined to yield a substituted imidazole of the formula

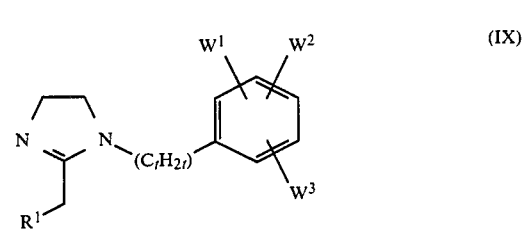
(IX)

The substituted imidazole of formula (IX) is treated with a suspension containing sodium hydride in dimethylformamide. The resulting mixture is treated with paraformaldehyde at a temperature preferably greater than 70° C. to yield a substituted ethenylimidazole of the formula

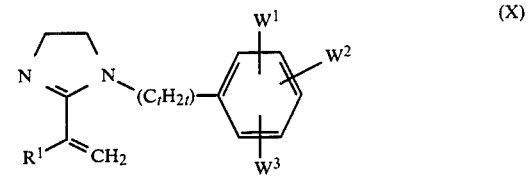
(X)

The substituted ethenylimidazole of formula (X) is reacted with imidazole under reflux conditions in an appropriate solvent to yield a substituted 4,5-dihydro-2[2-(imidazol-1yl)-1-substituted-ethenyl]imidazole of the formula

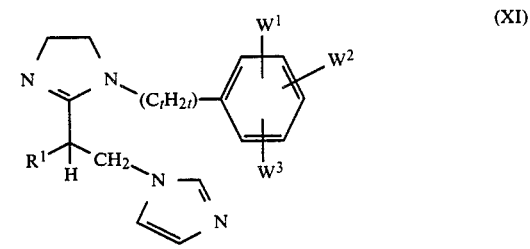
(XI)

METHOD C:

A 2-(imidazol-1-yl)ethanol of the formula

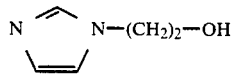 (XI)

is reacted with a toluenesulfonyl halide in an appropriate solvent under a nitrogen atmosphere at a temperature of from −20° C. to 0° C. to yield a 2-(imidazol-1-yl)-1-toluene-sulfonyloxyethane derivative of the formula

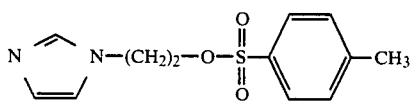 (XII)

The 2-(imidazol-1-yl)-1-toluenesulfonyloxyethane derivative of formula (XIII) is added to a mixture of a 1-substituted-4,5-dihydro-2-substituted imidazole of formula (VII), n-butyllithium and a copper(I)bromide-dimethylsulphide complex, under a nitrogen atmosphere at −78° C. The resulting mixture is allowed to warm to room temperature and the reaction mixture is quenched with saturated aqueous ammonium chloride to yield the compounds of formula (I).

The pharmaceutically acceptable addition salts of the compounds of the present invention may be prepared by conventional procedure, e.g. by reacting the free base in a suitable solvent, e.g. diethylether or ethanol, with a solution containing one equivalent of the desired acid in a suitable solvent, e.g. diethylether or ethanol. The salt generally precipitates from solution or is recovered by evaporation of the solvent. The compounds of formula (I) may form acid addition salts with inorganic acid such as hydrohalogenic acid (e.g. hydrochloric acid, hydrobromic acid), sulfuric acid, phosphoric acid, succinic acid, glyconic acid, glycolic acid, lactic acid, gluconic acid, tartaric acid, citric acid, maleic acid, malic acid, fumaric acid, methanesulfonic acid, p-toluenesulfonic acid, oxalic acid, ascorbic acid, benzoic acid or the like.

The temperatures at which the above reactions are conducted are not critical. It is preferred to conduct the above reaction at a temperature sufficient to allow the reaction to proceed towards completion. Such temperatures are readily ascertained by one of ordinary skill in the art.

The appropriate solvents employed in the above reactions are solvents in which the reactants are soluble but do not react with the reactants. The preferred solvents vary from reaction to reaction but are readily ascertained by one of ordinary skill in the art.

A preferred embodiment of the present invention includes compounds of the formula

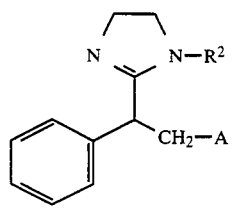 (XIII)

wherein A is imidazol-1-yl or substituted imidazol-1-yl and $R^2$ is substituted phenyl. A more preferred embodiment includes compounds of formula (XIII) wherein A is imidazol-1-yl or substituted imidazol-1-yl and $R^2$ is mono-or di-halophenyl. A most preferred embodiment of the present invention includes compounds of formula (XIII) wherein A is imidazol-1-yl or 2-methylimidazol-1-yl and $R^2$ is 2,4-dichlorophenyl or 2,4-dibromophenyl.

It should be noted that certain compounds of the formula

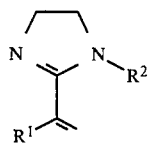 (XIV)

wherein $R^1$ and $R^2$ are above defined; are novel compounds and are active as anti-anaerobic agents. A preferred class of compounds of formula (XIV) are compounds wherein $R^1$ is phenyl and $R^2$ is substituted phenyl.

The compounds of the present invention may be administered topically, preferably in the form of a pharmaceutical composition adapted to such a route, and in a dose effective for the treatment intended.

Accordingly, the invention provides a class of novel pharmaceutical compositions comprising a therapeutically effective amount of one or more compounds of the present invention in association with one or more non-toxic, pharmaceutically acceptable carriers and/or diluents and/or adjuvants and if desired other active ingredients.

Representative carriers, diluents and adjuvants include for example water, lactose, gelatin, starches, magnesium stearate, talc, vegetable oils, gums, polyalkylene glycols, petroleum jelly, etc. The pharmaceutical compositions may be made up in a solid form such as granules, powders or suppositories or in a liquid form such as solutions, suspensions or emulsions. The pharmaceutical compositions may be subjected to conventional pharmaceutical operations such as sterilization and/or may contain conventional pharmaceutical adjuvants such as preservatives, stabilizers, wetting agents, emulsifiers, buffers, etc.

The dose administered and the treatment regiment will be dependent, for example, on the disease, the severity thereof, on the patient being treated and his response to treatment and therefore may be widely varied. Therapeutically effective amounts of the compounds of formula (I) are readily ascertained by one of ordinary skill in the art.

The following Examples are intended to further illustrate the present invention and not to limit the invention in spirit or scope.

EXAMPLE 1

1-(2-Chlorophenyl)-4,5-dihydro-2[2-(imidazol-1-yl)-1-phenylethyl]imidazole

A solution of ethyl 2-phenylprop-2-enoate (160 g, 0.45 mol), imidazole (36.7 g 0.54 mol) and tetramethylguanidine (2 g, 0.017 mol) in dry tetrahydrofuran (1 L) was heated at reflux temperature for 3 hours. The solvent was removed under reduced pressure and the residue was dissolved in dilute hydrochloric acid. The resulting aqueous solution was washed with ether, basified with dilute aqueous sodium hydroxide and extracted with chloroform. The organic phase was separated, dried over anhydrous magnesium sulfate, and concentrated under reduced pressure to yield ethyl 3-(imidazol-1-yl)-2-phenylpropanoate (90 g).

A mixture of ethyl 3-(imidazol-1-yl)-2-phenylpropanoate (89 g, 0.36 mol), concentrated hydrochloric acid (90 ml) and dioxan (140 ml) under an atmosphere of nitrogen, was heated at reflux temperature for 15 hours. The solvent was removed under reduced pressure and the resulting solid residue was washed with ether and dried in vacuo. The dried residue was dissolved in methanol and treated with decolorizing charcoal. The methanol solution was filtered and treated with ether to precipitate the hydrochloride salt of 3-(imidazol-1-yl)-2-phenylpropanoic acid (94 g).

A stirred suspension of the hydrochloride salt of 3-(imidazol-1-yl)-2-phenylpropanoic acid (1.47 g, 0.0058 mol) in dichloromethane (10 ml) was treated with triethylamine (0.8 ml, 0.0064 mol). The suspension was stirred for 30 minutes. Oxalylchloride (0.5 ml, 0.0064 mol) was added to the suspension and the resulting mixture was stirred for an additional 10 minutes. Dimethylformamide (0.5 ml 0.0064 mol) was added to the mixture to yield a clear solution. N-(2-chlorophenyl)ethanediamine (1 g 0.0058 mol) and triethylamine (0.8 ml 0.0064 mol) in dichloromethane (4 ml) were added with cooling to the clear solution. The resulting mixture was stirred for 30 minutes and then decanted into dilute aqueous sodium hydrogen carbonate. The organic phase was removed and the aqueous phase extracted with dichloromethane. The organic phases were combined, dried over anhydrous magnesium sulphate, and concentrated under reduced pressure to yield a residue which was chromatographed on silica gel eluting with methanol:dichloromethane (1:49) to yield $N^1$-[3-(imidazol-1-yl)2-phenylpropanoyl]-$N^2$-(2-chlorophenyl)ethanediamine as a gum. Treatment of this gum with ethereal hydrogen chloride yielded the hydrochloride salt of $N^1$-[3-(imidazol-1-yl)2-phenylpropanoyl]-$N^2$-(2-chlorophenyl)ethanediamine (1.94 g), m.p. 80°–85° C.

A mixture of $N^1$-[3-(imidazol-1-yl)-2-phenylpropanoyl]-$N^2$-(2-chlorophenyl)ethanediamine (1.6 g 0.0043 mol), methanesulfonic acid (20 ml) and phosphorous pentoxide (1.6 g, 0.0112 mol) were heated at 100° C. under an atmosphere of nitrogen for 18 hours. The reaction mixture was decanted into a mixture of ice and aqueous ammonia, and then extracted with dichloromethane. The organic phase was separated and concentrated under reduced pressure to yield a crude product which was chromatographed on silica gel using increasing proportions of methanol in dichloromethane to yield 1-(2-chlorophenyl)-4,5-dihydro-2[2-(imidazol-1-yl)-1-phenylethyl]imidazole which, upon treatment with ethereal hydrogen chloride, yielded a dihydrochloride salt of 1-(2-chlorophenyl)-4,5-dihydro-2-[2-(imidazol-1-yl)- 1-phenylethyl]imidazole (0.9 g) m.p. 118°–122° C., (Found C, 54.14; H, 5.30; N, 12.72. $C_{20}H_{21}Cl_3N_3$ requires C, 54.37; H, 5.25; N, 12.68) having the formula

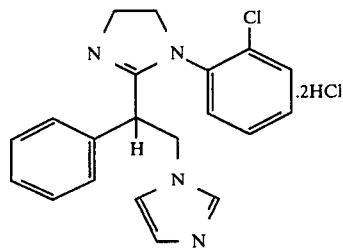

EXAMPLE 2–4

The procedure of Example 1 was conducted employing the appropriate starting materials to yield the following compounds:

EXAMPLE 2

1-(2,4-Dibromophenyl)-4,5-dihydro-2-[2-imidazol-1-yl)-1-phenylethyl]imidazole dihydrochloride (Found C, 42.41; H, 4.00; N, 10.02. $C_{20}H_{19}N_4Br_2Cl_2.H_2O$ requires C, 42.51; H, 3.92; N, 9.91) having the formula

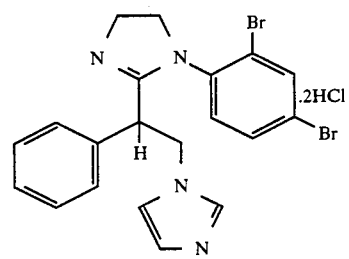

EXAMPLE 3

1-(2,4-Dichlorophenyl)-4,5-dihydro-2-[2-(imidazol-1-yl)-1-phenylethyl]imidazole hydrochloride (Found C, 48.35; H, 5.25; N, 11.02. $C_{20}H_{18}N_4Cl_4.2H_2O$ requires C, 48.60; H, 5.30; N, 11.33) having the formula

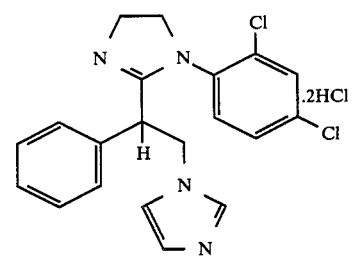

EXAMPLE 4

4,5-Dihydro-2-[2-(imidazol-1-yl)-1-phenylethyl]-1-(3-trifluoromethylphenyl)imidazole hydrochloride m.p. 141°–143° C. (Found C, 51.46; H, 4.98; N, 11.48. $C_{21}H_{21}N_4F_3Cl_2.2H_2O$ requires C, 51.12; H, 5.11; N, 11.36) having the formula

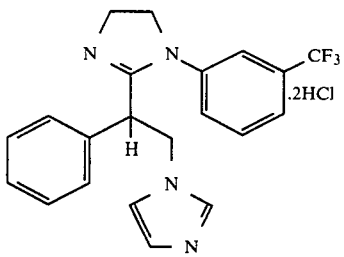

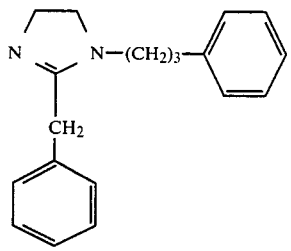

EXAMPLE 5

1-(2,4-Dichlorophenylmethy)1-4,5-dihydro-2-phenyl-methylimidazole

Tolazoline (16 g, 0.1 mol) in dimethylformamide (40 ml) was added dropwise to a suspension of sodium hydride (80% dispersion in mineral oil, 3 g, 0.1 mol) in dimethylformamide (40 ml) under a nitrogen atmosphere. After stirring at 20° C. for 30 minutes and at 65° C. for an additional 30 minutes, a solution of 2,4-dichlorobenzyl chloride (19.5 g, 0.1 mol) in dimethylformamide was added dropwise to the reaction mixture over a period of 2.5 hours. The mixture was heated to 80°–90° C. for 5 hours, cooled and concentrated under reduced pressure. Water was added to the residue and the resulting mixture was extracted with ethyl acetate. The organic phase was separated, washed with brine and dried over anhydrous magnesium sulphate. The solvent was removed under reduced pressure yielding a residue which was chromatographed on silica gel eluting with ammonia/methanol/ethyl acetate (3:12:85) to yield as a colorless oil, 1-(2,4-dichlorophenylmethyl)-4,5-dihydro-2-phenylmethylimidazole (16 g). Treatment of the oil with ethereal hydrogen chloride yielded the hydrochloride salt of 1-(2,4-dichlorophenylmethyl)-4,5-dihydro-2-phenylmethyl imidazole m.p. 185°–189° C. (Found C, 56.75; H, 4.91; N, 7.71. $C_{17}H_{17}Cl_3N_2.\frac{1}{4}H_2O$ requires C, 56.70; H, 5.58; N, 7.77) having the formula

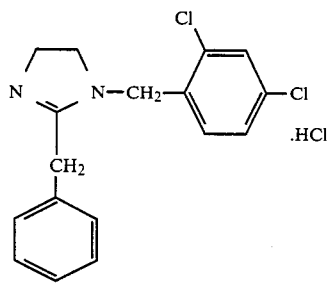

EXAMPLE 6

4,5-Dihydro-2-phenylmethyl-1-(3-phenylpropyl)imidazole

The procedure of Example 5 was employed utilizing 3-bromo-1-phenylpropane in lieu of 2,4-dichlorobenzyl chloride to yield 4,5-dihydro-2-phenylmethyl-1-(3-phenyl propyl)imidazole (Found C, 79.46; H, 8.25; N, 9.70. $C_{19}H_{22}N_2.\frac{1}{4}H_2O$ requires C, 79.44; H, 8.01; N, 9.75) having the formula

EXAMPLE 7

4,5-Dihydro-1-n-octyl-2-phenylmethylimidazole

A solution of toluenesulphonic acid (3 g, 0.0159 mol) in a mixture of water:isopropanol (20 ml, 1:1) was cooled to 0° C. and treated with N-(n-octyl)ethanediamine (3 g, 0.0175 mol) in isopropanol (10 ml). The solution was allowed to warm to room temperature and the solvent removed under reduced pressure to yield a solid which was recrystallized from isopropanol, to yield N-(n-octyl)-ethanediamine tosylate (3 g) as white plates, m.p. 80°–85° C.

A mixture of N-(n-octyl)-ethanediamine tosylate (10 g, 0.029 mol) and benzyl cyanide (0.9 ml, 0.029 mol) was heated at 200° C. until evolution of ammonia ceased. The reaction mixture was cooled to 50° C. and treated with aqueous sodium hydroxide (15 ml, 5M). The resulting mixture was stirred for 15 minutes and then extracted with dichloromethane. The organic phase was separated, washed with water, and dried over anhydrous magnesium sulphate. Th solvent was removed under reduced pressure to yield a gum which was chromatographed on silica gel using increasing proportions of methanol in dichloromethane to yield 4,5-dihydro-1-n-octyl-2-phenylmethylimidazole (7.8 g) having the formula

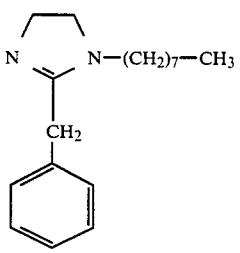

EXAMPLE 8

1-(2,4-Dichlorophenylmethyl)-4,5-dihydro-2-(1-phenylethenyl)imidazole 1-(2,4-Dichlorophenyl)methyl-4,5-dihydro-2-phenylmethylimidazole (3.19 g, 0.1 mol) was added to a slurry of sodium hydride (80% dispersion in mineral oil, 0.3 g, 0.01 mol) in dry dimethylformamide (15 ml) and the mixture was stirred at room temperature for 30 minutes. Paraformaldehyde (3 g, 0.01 mol) was added to the reaction mixture and the resulting mixture was heated at 70° C. for 6 hours. The reaction mixture was cooled, water was added and the resulting mixture was extracted with ether. The organic phase was separated, washed with brine, dried over anhydrous magnesium sulphate, and concentrated under reduced pressure. The resulting residue was chromatographed on silica gel in ammonia/methanol/ethyl acetate (1:4:45) to yield 1-(2,4-dichlorophenylmethyl)-4,5-dihydro-2-(1-phenylethenyl)imidazole (2.6 g), (δ (CDCl₃) 3.3 (2H, t,J=6 Hz), 3.95 (2H, t,J=6 Hz), 4.1 (2H,s), 5.65 (1H, s), 5.8 (1H, s), and 7.0–7.5 (8H, m) p.p.m. having the formula

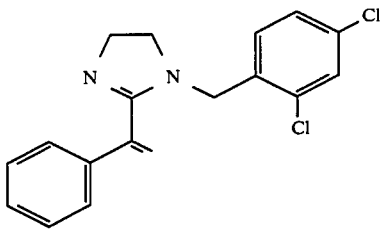

EXAMPLES 9–14

The procedure of Example 8 was conducted employing the appropriate starting materials to yield the following compounds:

EXAMPLE 9

4,5-Dihydro-2-(1-phenylethenyl)-1-(3-phenylpropyl)imidazole (δ(CDCl₃) 2.35(2 H,q, J=5 Hz), 2.65 (2H, t,J=5 Hz), 3.35 (2H, t, J=6 Hz), 3.9 (2H, t, J=6 Hz), 5.55 (1H, s), 5.75 (1H, s) and 7.0–7.45 (10H, m) p.p.m.) having the formula

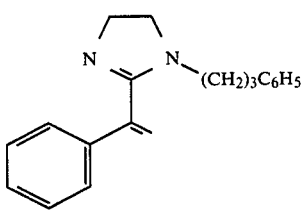

EXAMPLE 10

4,5-Dihydro-1-n-hexyl-2-(1-phenylethenyl)imidazole (δ(CDCl₃), 0.87 (3H, t), 0.93–141 (12H, m), 2.83 (2H, t), 3.37 (2H, t), 3.90 (2H, t), 5.57 (1H, s) and 7.22–8.33 (8H, m) p.p.m.) having the formula

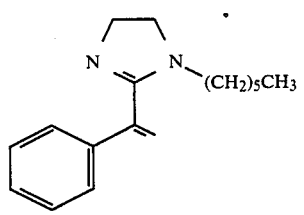

EXAMPLE 11

1-(2,4-Dichlorophenyl)-4,5-dihydro-2-(1-phenylethenyl)imidazole (δ(CDCl₃) 3.80 (2H, t), 4.07 (2H, t), 5.57 (1H, s), 5.70 (1H, s) and 6.80–7.44 (8H, m) p.p.m.) having the formula

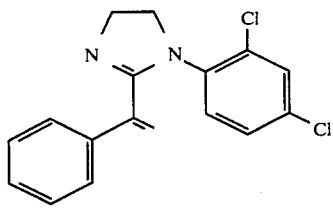

EXAMPLE 12

4,5-Dihydro-1-(2,4-dimethylphenyl)-2-(1-phenylethenyl) imidazole (δ(CDCl₃) 2.07 (3H,s), 2.24 (3H, s), 3.69 (2H, bs), 4.07 (2H, t), 5.52 (1H, s), 5.60 (1H, s) 6.76–7.37 (8H, m) p.p.m.) having the formula

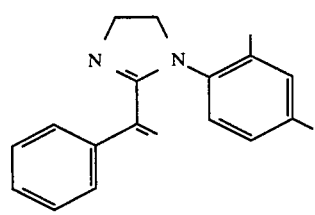

EXAMPLE 13

4,5-Dihydro-1-n-hexyl-2-(1-phenylethenyl)imidazole (δ(CDCl₃) 0.83 (3H,t,J=7.5 Hz), 1.05–1.42 (8H,m), 2.84 (2H, t, J=7.5 Hz), 3.36 (2H, t, J=10 Hz), 3.88 (2H, t, J=10 Hz), 5.56 (1H, s), 5.74 (1H, s) and 7.25–7.48 (5H, m) p.p.m.)

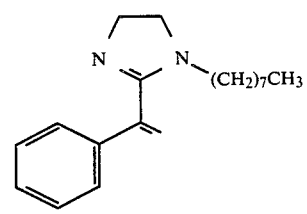

EXAMPLE 14

1-n-Decyl-4,5-dihydro-2-(1-phenylethenyl)imidazole (δ(CDCl₃) 0.88 (3H, t, J=7.5 Hz), 1.40–1.80 (16H,m), 2.82 (2H, t, J=7.5 Hz), 3.35 (2H, t, J=10 Hz), 3.87 (2H, t, J=10 Hz), 5.56 (1H, s), 5.75 (1H, s) and 7.1–7.45 (5H, m) p.p.m.)

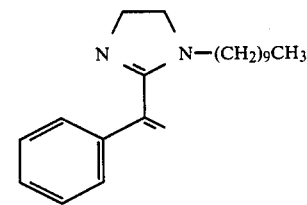

EXAMPLE 15

1-(2,4-Dichlorophenylmethyl)-4,5-dihydro-2-[2-(imidazol-1-yl)-1-phenylethyl]imidazole A solution of 1-(2,4-dichlorophenylmethyl)-4,5-dihydro-2-(1-phenylethenyl)imidazole (100 mg, 0.003 mol) and imidazole (100 mg) in ethanol (20 ml) was heated at reflux for 18 hours. The solvent was removed under reduced pressure and the residue was dissolved in ether. The resulting ethereal solution was washed with water, dried over anhydrous magnesium sulphate and concentrated under reduced pressure. The residue was chromatographed on silica gel in ammonia/methanol/ethyl acetate (1:4:45) to yield a gum which was treated with ethereal hydrogen chloride, to yield the dihydrochloride salt of 1-(2,4-dichlorophenylmethyl)-4,5-dihydro-2-[2-(imidazol-1-yl)-1-phenylethyl]imidazole (110 mg) m.p. 120°–135° C., (Found C, 53.64; H, 4.60, N. 11.71. $C_{21}H_{22}Cl_4N_4$ requires C, 53.40; H, 4.66; N, 11.86) having the formula

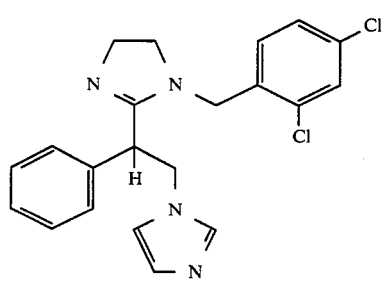

EXAMPLES 16–26

The procedure of Example 14 was conducted employing the appropriate starting materials to yield the following compounds:

EXAMPLE 16

1-(2,4-Dichlorophenylmethyl)-4,5-dihydro-2-[1-phenyl-2-(pyrazol-1-yl)ethyl]imidazole dihydrochloride m.p. 65°–70°, (Found C, 53.04; H, 4.95; N, 11.78. $C_{21}H_{22}Cl_4N_4$ requires C, 53.39; H, 4.66; N, 11.86) having the formula

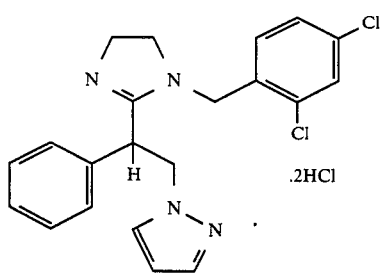

EXAMPLE 17

1-(2,4-Dichlorophenylmethyl)-4,5-dihydro-2-[1-phenyl-2-(1,2,4-triazol-1-yl)ethyl]imidazole dihydrochloride m.p. 150°–155° C., (Found: C, 50.90; H, 4.63; N, 14.3. $C_{20}H_{21}Cl_4N_5$ requires C, 50.74; H, 4.44; N, 14.3) having the formula

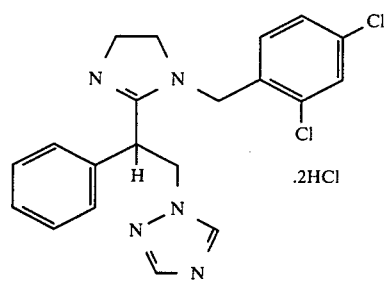

EXAMPLE 18

4,5-Dihydro-2-[2-(imidazol-1-yl)-1-phenylethyl]-1-(3-phenylpropyl)imidazole dihydrochloride m.p. 45°–58° C., (Found: C, 63.21; H, 7.19; N, 12.0. $C_{23}H_{28}Cl_2N_4.\frac{1}{4}H_2O$ required C, 63.37; H, 6.54; N, 12.0) having the formula

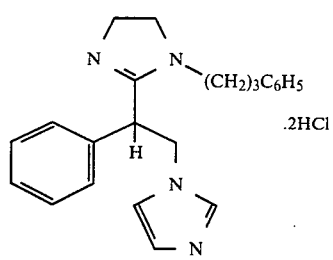

EXAMPLE 19

4,5-Dihydro-2-[2-(imidazol-1-yl)-1-phenylethyl]-1-n-octylimidazole dihydrochloride (Found: C, 61.21; H, 8.02; N, 12.91. $C_{22}H_{34}Cl_2N_4.\frac{1}{2}H_2O$ requires C, 60.82; H, 8.1; N, 12.90) having the formula

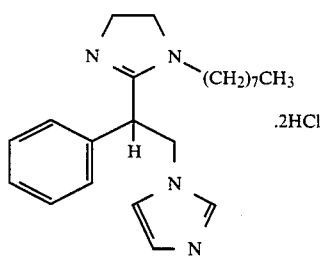

EXAMPLE 20

1-(2,4-Dichlorophenyl)-4,5-dihydro-2-[1-phenyl-2-(1,2,4-triazol-1-yl)ethyl]imidazole m.p. 78°–82° C., (Found C, 58.54; H, 4.31; N, 17.80. $C_{19}H_{17}Cl_2N_5.\frac{1}{4}H_2O$ requires C, 58.30; H, 4.51; N, 17.92) having the formula

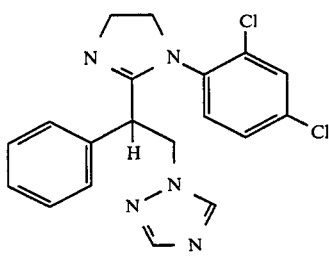

EXAMPLE 21

1-(2,4-Dichlorophenyl)-4,5-dihydro-2-[2-(2-methylimidazol-1-yl)-1-phenylethyl]imidazole dihydrochloride (Found C, 50.86; H, 5.13; N, 11.15. $C_{21}H_{22}Cl_4N_4.3/2$ $H_2O$ requires C, 50.51; H, 5.05; N, 11.22) having the formula

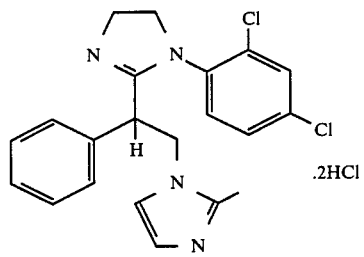

EXAMPLE 22

1-(2,4-Dichlorophenyl)-4,5-dihydro-2-[1-phenyl-2-(2-thiomethylimidazol-1-yl)ethyl]imidazole dihydrochloride (Found C, 48.37; H, 4.63; N, 10.60. $C_{21}H_{22}Cl_4N_4S.H_2O$ requires C, 48.27; H, 4.63; N, 10.73) having the formula

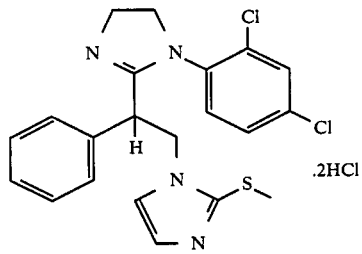

EXAMPLE 23

1-(2,4-Dichlorophenyl)-4,5-dihydro-2-[2-(4,5-dihydro-2-methylimidazol-1-yl)-1-phenylethyl]imidazole dihydrochloride (Found C, 50.52; H, 5.24; N, 11.09. $C_{21}H_{24}Cl_4N_4.3/2$ $H_2O$ requires C, 50.31; H, 5.43; N, 11.18) having the formula

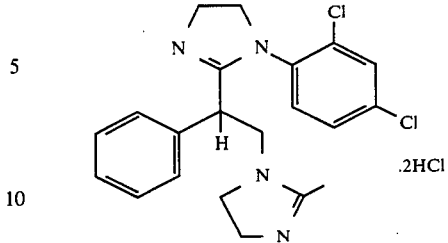

EXAMPLE 24

4,5-Dihydro-1-(2,4-dimethylphenyl)-2-[2-(imidazol-1-yl)-1-phenylethyl]imidazole dihydrochloride (Found C, 61.19; H, 6.57; N, 12.57. $C_{22}H_{26}Cl_2N_4.H_2O$ requires C, 60.69; H, 6.48; N, 12.87) having the formula

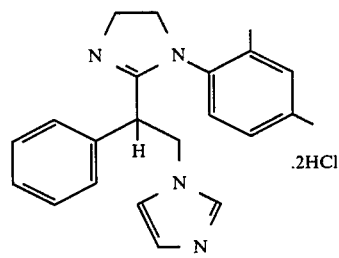

EXAMPLE 25

4,5-Dihydro-1-n-hexyl-2-[2-(imidazol-1-yl)-1-phenylethyl]imidazole hydrochloride ($\delta(d_6DMSO)$ 0.75 (3H, t, J=7H$_2$), 0.93-1.33 (8H, m), 3.29-3.55 (2H, m), 3.83 (2H, 6.5), 4.60 (1H, dd), 5.02 (1H, m), 5.19 (1H, dd), 7.12 (1H, s), 7.38-7.62 (6H, M) and 8.17 (1H, s) p.p.m.) having the formula

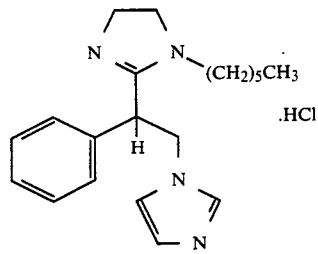

EXAMPLE 26

1-n-Decyl-4,5-dihydro-2-[2-(imidazol-1-yl)-1-phenylethyl]imidazole dihydrochloride ($CDCl_3$ 0.94 (3H, t, J=7.5 Hz), 1.00-1.45 (16H, m), 3.05 (2H, m), 3.50 (2H, t, J=10 Hz), 3.98 (1H, t, J=6 Hz), 4.10 (2H, t, J=10 Hz), 4.55 (1H, dd, J=6 and 14 Hz), 5.08 (1H, dd, J=6 and 14 Hz), 7.25 (1H, s), 7.46 (1H, s) and 7.60-7.90 (6H, m) p.p.m.) having the formula

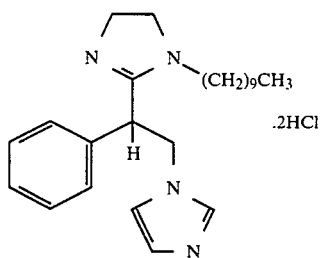

EXAMPLE 27

1-(2,4-Dichlorophenyl)-4,5-dihydro-2-[3-(imidazol-1-yl)-1-phenylpropyl]imidazole To a stirred solution of 2-(imidazol-1-yl)ethanol (1.9 g, 0.0156 mol), triethylamine (2.8 ml, 0.0187 mol), and 4-N,N-dimethylaminopyridine (20 mg) in dichloromethane (20 ml) at a temperature of −78° C. under nitrogen atmosphere, was added p-toluenesulphonyl chloride (3.6 g, 0.0187 mol) in dichloromethane (10 ml). The reaction mixture was allowed to warm to −10° C. and was then quenched by the addition of saturated aqueous sodium hydrogen carbonate. The organic phase was separated and the aqueous phase extracted with dichloromethane. The organic phases were combined, washed with brine, dried over anhydrous magnesium sulphate and concentrated under reduced pressure to yield colorless crystals of 2-(imidazol-1-yl)-1-toluenesulphonyloxyethane (4.23 g). n-Butyllithium (3.9 ml, 0.0059 mol, 1.5M in hexane) was added to a stirred solution of 1-(2,4-dichlorophenyl)-4,5-dihydro-2-phenylmethylimidazole (1.5 g, 0.0049 mol) in dry tetrahydrofuran (10 ml) at −78° C. under a nitrogen atmosphere. Copper(I)bromide-dimethyl sulphide complex (50 mg, 0.0024 mol) was added to the reaction mixture. After a period of one hour, a solution of 2-(imidazol-1-yl)-1-toluenesulphonyloxyethane (2 g, 0.0072 mol) in tetrahydrofuran (7 ml) was added to the reaction mixture. The resulting mixture was allowed to warm to room temperature and allowed to react for 15 hours before being quenched with saturated aqueous ammonium chloride. The phases were separated and the aqueous phase extracted with ethyl acetate. The organic phases were combined, washed with brine, dried over anhydrous magnesium sulphate and concentrated under reduced pressure to yield an oil which was chromatographed on silica gel with ammonia/methanol/ethyl acetate (1:4:45) to yield 1-(2,4-dichlorophenyl)-4,5-dihydro-2-[3-(imidazol-1-yl)-1-phenylpropyl]imidazole (1 g) which upon treatment with ethereal hydrogen chloride yielded the hydrochloride salt of 1-(2,4-dichlorophenyl)-4,5-dihydro-2-[3-(imidazol-1-yl)-1-phenylpropyl]imidazole. (Found C, 49.00; H, 5.03; N, 10.76. $C_{21}H_{22}N_4Cl_4.9/4\ H_2O$ requires C, 49.19; H, 5.21; N, 10.93) having the formula

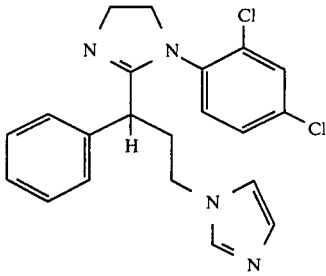

The anti-anaerobic activity of the compounds of the present invention is demonstrated by the following examples:

EXAMPLE 28

The screening panel utilized in this Example consisted of 5 strains of *Bacteroides fragilis*. All assays were carried out in 96 well microtitre plates. If an isolate was obtained from either a culture collection or clinical source, the isolate was immediately inoculated into Wilkins-Chalgren broth (Oxoid) and incubated at 37° C. in an anaerobic chamber in an atmosphere of 85% nitrogen, 10% carbon dioxide, and 5% hydrogen for 48 hours. At the end of this time, the viable count was about $10^{12}$ organisms/ml broth. A 1 ml aliquot of each culture was placed in an ampoule and quick frozen in an acetone-dry-ice mixture and stored in liquid nitrogen. When an inoculum was utilized in an assay, one of the ampoules was thawed and diluted with fresh broth to yield a suspension having a count of $5 \times 10^5$ organisms/ml. 100 μl of the suspension was inoculated into each well of the microtitre plate.

2 mg of the test compound was dissolved in 0.2 ml of a suitable solvent such as dimethylsulphoxide, polyethylene glycol 200 or methanol. The solution was diluted with 4.8 ml of water to yield a solution having a concentration of 400 ml/L. Doubling dilutions of this stock were prepared to give a range of concentrations from 1.6–200 mg/L. 100 μl aliquots of each concentration are then placed in the wells of the microtitre plate containing the inoculum, to produce a final concentration range of 0.8–100 mg/L. Metronidazole was employed as a positive control and a solvent/water mixture was employed as a negative control. After addition of the test solution, the final inoculum level is $10^5$ cells/ml. The plates were incubated for 48 hours at 37° C. in the anaerobic chamber. The Minimum Inhibitory Concentration (MIC) was read visually. The MIC is defined as the lowest concentration at which there is no detectable growth. The Minimum Bactericidal Concentration (MBC) was determined by taking a 50 μl aliquot from each well and placing it in fresh medium. The MBC is defined as the lowest concentration at which there is less than 5 colonies (i.e., 99.9% reductin in viable count) after 48 hours incubation. The MIC and MBC values for each compound tested and the respective MIC and MBC value for metronidazole are indicated by Table I. The MIC and MBC value for the negative control that was assayed along with each compound tested was greater than 100 mg/L. The MIC and MBC values in Table I are expressed in mg/L. A blank in the Table represented by a "—" indicates that the assay was not conducted using the strain indicated.

The strains of *Bacteroides fragilis* utilized in the above procedure are identified in Table I by letter in accordance with the following legend:

| STRAIN | ORGANISM |
|---|---|
| A | B. Fragilis NCTC 10581 |
| B | B. Fragilis NCTC 9343 |
| C | B. Fragilis NCTC 9344 |
| D | B. Fragilis ATCC 11295 |
| E | B. Fragilis WS-1* |

*Obtained from St. Thomas Hospital Medical School, London, United Kingdom

TABLE I

| COMPOUND OF EXAMPLE NO. | STRAIN A | | B | | C | | D | | E | |
|---|---|---|---|---|---|---|---|---|---|---|
| | MIC | MBC | MIC | MBC | MIC | MBC | MIC | MBC | MIC | MBC |
| 1 | 3.1 | — | 12.5 | — | 6.2 | — | 6.2 | — | 12.5 | — |
| Metronidazole | 0.6 | 1.2 | 1.2 | 1.2 | 0.6 | 1.2 | 10 | 10 | 0.6 | 0.6 |
| 2 | 0.8 | 3.1 | 3.1 | 12.5 | 1.5 | 50 | 1.5 | 12.5 | 0.8 | 2.5 |
| Metronidazole | 0.6 | 1.2 | 0.6 | 1.2 | 0.6 | 0.6 | 10 | 10 | 1.2 | 1.2 |
| 3 | 0.8 | 0.8 | 1.5 | 1.5 | 0.8 | 0.8 | 0.8 | 0.8 | 1.5 | 3.1 |
| Metronidazole | 0.8 | 0.8 | 1.5 | 1.5 | 0.8 | 0.8 | 0.8 | 0.8 | 1.5 | 3.1 |
| 4 | 6.2 | — | 12.5 | — | 12.5 | — | 12.5 | — | 12.5 | — |
| Metronidazole | 0.6 | 1.2 | 1.2 | 1.2 | 0.6 | 1.2 | 10 | 10 | 0.6 | 0.6 |
| 15 | 3.1 | — | 3.1 | — | 3.1 | — | 3.1 | — | 6.2 | — |
| Metronidazole | 0.6 | — | 0.6 | — | 1.2 | — | 10.0 | — | 0.3 | — |
| 16 | 2.5 | — | — | — | 3.1 | — | — | — | 100 | — |
| Metronidazole | 0.6 | — | — | — | 0.3 | — | — | — | 0.3 | — |
| 17 | 50 | — | — | — | 50.0 | — | 50.0 | — | 50.0 | — |
| Metronidazole | 0.6 | — | — | — | 0.3 | — | 5.0 | — | 0.3 | — |
| 18 | 25 | — | 25 | — | 50 | — | 25 | — | 25 | — |
| Metronidazole | 0.8 | 2.5 | 0.8 | 0.8 | 0.8 | 3.1 | 12.5 | 12.5 | 0.8 | 0.8 |
| 19 | 12.5 | 25 | 3.1 | 6.2 | 12.5 | 25 | 25 | 100 | 12.5 | 12.5 |
| Metronidazole | 0.8 | 2.5 | 0.8 | 0.8 | 0.8 | 3.1 | 12.5 | 12.5 | 0.8 | 0.8 |
| 20 | 12.5 | — | 25.0 | — | 25.0 | — | 25.0 | — | 25.0 | — |
| Metronidazole | 0.6 | 0.6 | 0.6 | 0.6 | 0.6 | 0.6 | 10 | 10 | 1.2 | 1.2 |
| 21 | 12.5 | 12.5 | 1.5 | 1.5 | 0.8 | 0.8 | 3.1 | 0.8 | 0.8 | 0.8 |
| Metronidazole | 0.6 | 1.2 | 0.6 | 0.6 | 0.6 | 1.2 | 10 | 10 | 0.6 | 0.6 |
| 22 | 6.2 | 6.2 | 1.5 | 1.5 | 3.1 | 3.1 | 3.1 | 3.1 | 3.1 | 3.1 |
| Metronidazole | 0.6 | 1.2 | 0.6 | 0.6 | 0.6 | 1.2 | 10 | 10 | 0.6 | 0.4 |
| 23 | 1.5 | 1.5 | 1.5 | 3.1 | 1.5 | 1.5 | 1.5 | 1.5 | 0.8 | 1.5 |
| Metronidazole | 0.6 | 1.2 | 0.6 | 0.6 | 0.6 | 1.2 | 10 | 10 | 0.6 | 0.6 |
| 24 | 25.0 | — | 12.5 | — | 12.5 | — | 12.5 | — | 25.0 | — |
| Metronidazole | 0.6 | — | 0.6 | — | 0.6 | — | 10 | — | 1.2 | — |
| 25 | 25.0 | — | 100.0 | — | 100.0 | — | 100.0 | — | 100.0 | — |
| Metronidazole | 0.6 | — | 0.6 | — | 0.3 | 0 | 10.0 | — | 0.4 | — |
| 26 | 2.1 | 3.1 | — | — | 3.1 | 3.1 | 3.1 | 50 | 3.1 | 3.1 |
| Metronidazole | 1.2 | 1.2 | — | — | 0.6 | 1.2 | 10 | 10 | 1.2 | 2.5 |
| 27 | 100 | — | 100 | — | 100 | — | 100 | — | 12.5 | — |
| Metronidazole | 0.8 | — | 1.5 | — | 1.5 | — | 12.5 | — | 1.5 | — |

EXAMPLE 29

Conducting the procedures described in Example 28, the anti-anaerobic activity of the compound of Example 3 was determined utilizing an additional 12 strains. The MIC against *Trichomonas vaginalis* was determined in accordance with the method described in Example 28 except that the organisms are grown in Diamonds Medium and the MIC is defined as the lowest concentration at which no mobile organisms are viable microscopically. The data collected is represented in the following Table. A blank in the Table represented by a "—" indicates that the assay was not conducted using the strain indicated.

TABLE 2

| STRAIN | COMPOUND OF EXAMPLE 3 | | METRONIDAZOLE | |
|---|---|---|---|---|
| | MIC | MBC | MIC | MBC |
| *Clostridium perfringens* NCTC 523 | 0.8 | 3.1 | 0.08 | 1.2 |
| *Cl. perfringens* NCTC 8237 | 3.1 | 3.1 | 10 | 10 |

TABLE 2-continued

| STRAIN | COMPOUND OF EXAMPLE 3 | | METRONIDAZOLE | |
|---|---|---|---|---|
| | MIC | MBC | MIC | MBC |
| *Campl. fetus* ATCC 29428 | 1.5 | 6.2 | 10 | 10 |
| *Fuso. necrophorum* ATCC 11295 | 3.1 | 6.2 | 10 | 10 |
| *Peptococc. magnus* ATCC 29328 | 1.5 | 6.2 | 0.6 | 10 |
| *P. prevotti* ATCC 9321 | 3.1 | 12.5 | 1.2 | 2.5 |
| *Peptostrepto anaerobicus* ATCC 27337 | 1.5 | 3.1 | 0.3 | 0.3 |
| *Propionibacterium acnes* NCTC 737 | 0.8 | 3.1 | 10 | 10 |
| *P. acnes* NCTC 7337 | 0.8 | 0.8 | 10 | 10 |
| *T. vaginalis* | 3.1 | — | 0.6 | — |

Although this invention has been described with respect to specific modification, the details thereof are not to be construed as limitations, for it will be apparent that various equivalents, changes and modification may be restored and modification may be resorted to without departing from the spirit and scope thereof and it is understood that such equivalent embodiments are intended to be included therein.

What is claimed is:

1. A compound of the formula

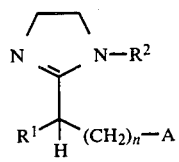

wherein

A is imidazol-1-yl, pyrazol-1-yl, 1,2,4-triazol-1-yl, 4,5-dihydroimidazol-1-yl, substituted imidazol-1-yl or substituted 4,5-dihydroimidazol-1-yl wherein the imidazol-1-yl or 4,5-dihydroimidazol-1-yl is substituted with a substituent selected from the group consisting of $C_1$–$C_4$ alkylthio and $C_1$–$C_4$ alkyl;

$R^1$ is phenyl or substituted phenyl having from 1 to 3 substituents independently selected from the group consisting of $C_1$–$C_4$ alkyl and halogen;

$R^2$ is $C_1$–$C_1$ alkyl, phenyl, phenyl ($C_1$–$C_4$ alkyl), substituted phenyl having from 1 to 3 substitutents independently selected from the group consisting of $C_1$–$C_4$ alkyl, halogen and trifluoromethyl; or a

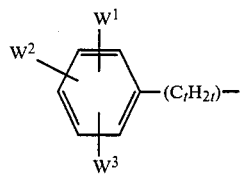

group wherein t is an integer of from 1 to 4 and $W^1$, $W^2$ and $W^3$ are independently hydrogen, $C_1$–$C_4$ alkyl, halogen or trifluoromethyl;

n is an integer 1 or 2;

or a pharmaceutically acceptable acid addition salt thereof.

2. A compound according to claim 1 wherein $R^1$ is phenyl.

3. A compound according to claim 2 wherein A is imidazol-1-yl or substituted imidazol-1-yl and $R^2$ is substituted phenyl.

4. A compound according to claim 3 wherein $R^2$ is substituted phenyl having 1 or 2 halogen substituents.

5. A compound according to claim 4 wherein $R^2$ is 2,4-dichlorophenyl or 2,4-dibromophenyl.

6. A compound according to claim 5 of the formula

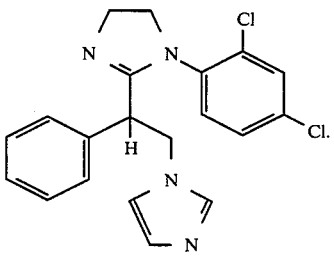

* * * * *